United States Patent [19]

Engelskirchen et al.

[11] Patent Number: 4,618,582
[45] Date of Patent: Oct. 21, 1986

[54] PROCESS FOR PRODUCING XANTHOMONAS BIOPOLYMERS

[75] Inventors: Konrad Engelskirchen, Meerbusch; Werner Stein, Düsseldorf; Michael Bahn, Hilden; Ludwig Schieferstein, Oberhausen; Joachim Schindler, Hilden; Rolf Schmid, Düsseldorf, all of Fed. Rep. of Germany

[73] Assignee: Henkel Kommanditgesellschaft auf Aktien, Duesseldorf, Fed. Rep. of Germany

[21] Appl. No.: 346,591

[22] Filed: Feb. 8, 1982

[30] Foreign Application Priority Data

Feb. 16, 1981 [DE] Fed. Rep. of Germany ....... 3105556

[51] Int. Cl.$^4$ .................. C12P 19/06; C12N 1/26; C12N 1/20; C12R 1/64
[52] U.S. Cl. .................................... 435/104; 435/248; 435/249; 435/253; 435/910
[58] Field of Search .............. 435/248, 249, 250, 253, 435/101, 104, 910

[56] References Cited

U.S. PATENT DOCUMENTS

| 3,000,790 | 9/1961 | Jeanes et al. | 195/31 |
| 3,020,206 | 2/1962 | Patton et al. | 195/31 |
| 3,251,749 | 5/1966 | Lipps, Jr. | 195/31 |
| 3,271,267 | 9/1966 | Weber et al. | 195/31 |
| 3,281,329 | 10/1966 | Lipps, Jr. | 195/31 |
| 3,391,060 | 7/1968 | McNeely | 195/31 |
| 3,391,061 | 7/1968 | McNeely | 195/31 |
| 3,427,226 | 2/1969 | McNeely | 195/31 |
| 3,433,708 | 3/1969 | McNeely | 195/31 |
| 3,455,786 | 7/1969 | Miescher | 195/31 |
| 3,565,763 | 2/1971 | Cadmus et al. | 195/31 |
| 3,594,280 | 7/1971 | Colin et al. | 195/31 |
| 4,102,744 | 7/1978 | McCoy et al. | 435/249 X |
| 4,119,546 | 10/1978 | Wernau | 252/8.55 |
| 4,352,882 | 10/1982 | Maury | 435/104 X |

Primary Examiner—David M. Naff
Attorney, Agent, or Firm—Ernest G. Szoke; Henry E. Millson, Jr.

[57] ABSTRACT

In the aerobic culture of microorganisms of the Xanthomonas genus in fermentation media, the use of water-in-oil emulsions in the media minimizes viscosity problems and enhances yields of Xanthomonas biopolymers. Preferably, the emulsion is formed with a surfactant and the microorganism is *Xanthomonas campestris*.

10 Claims, No Drawings

PROCESS FOR PRODUCING XANTHOMONAS BIOPOLYMERS

BACKGROUND OF THE INVENTION

Hydrophilic colloids produced by various species of Xanthomonas bacteria are exocellular heteropolysaccharides containing mannose, glucose, glucuronic acid, o-acetyl mannose groups, and pyruvic acid residues ketalically linked to certain of the terminal D-mannose residues in the polysaccharide molecule.

Xanthan gum, also referred to as xanthan and as polysaccharide B-1459, is an exocellular heteropolysaccharide which is produced by Xanthomonas campestris.

The exocellular heteropolysaccharides are produced by certain species of Xanthomonas bacteria when these bacteria are grown aerobically in aqueous nutrient solutions. Such nutrient solutions contain, in addition to the usual growth promoting ingredients, a water soluble carbohydrate as a carbon source that can be readily assimilated by the bacteria, e.g. glucose.

The Xanthomonas heteropolysaccharides exhibit marked thickening properties as well as thixotropy in aqueous solutions, and are used extensively in various industries. Due to their non-toxic properties they have many applications in the food industry, as well as other industrial applications. Recently, they have been used for the secondary and tertiary recovery of oil deposits.

Processes for the preparation of such heteropolysaccharides are described in the following patents:

| Document No. | Date | Title |
| --- | --- | --- |
| U.S. Pat. No. 3,000,790 | Sept. 19, 1961 | Method of Producing an Atypically Salt-Responsive Alkali-Deacetylated Polysaccharide. |
| U.S. Pat. No. 3,020,206 | Feb. 6, 1962 | Process for Synthesizing Polysaccharides. |
| U.S. Pat. No. 3,251,749 | May 17, 1966 | Fermentation Process for Preparing Polysaccharides. |
| U.S. Pat. No. 3,271,267 | Sept. 6, 1966 | Biochemical Synthesis of Industrial Gums. |
| U.S. Pat. No. 3,281,329 | Oct. 25, 1966 | Fermentation Process for Producing a Heteropolysaccharide. |
| U.S. Pat. No. 3,391,060 | July 2, 1968 | Process for Producing a Polysaccharide. |
| U.S. Pat. No. 3,391,061 | July 2, 1968 | Process for Producing Polysaccharides. |
| U.S. Pat. No. 3,427,226 | Feb. 11, 1969 | Process for Preparing Polysaccharides. |
| U.S. Pat. No. 3,433,708 | March 18, 1969 | Process for Producing a Polysaccharide. |
| U.S. Pat. No. 3,455,786 | July 15, 1969 | Process for the Production of Polysaccharide Gum Polymers |
| U.S. Pat. No. 3,565,763 | Feb. 23, 1971 | Nitrogen Source for Improved Production of Microbial Polysaccharides. |
| U.S. Pat. No. 3,594,280 | July 20, 1971 | Processes for Carrying Out Polysaccharide-Producing Fermentations. |
| U.S. Pat. No. 4,119,546 | Oct. 10, 1978 | Process for Producing Xanthomonas Hydrophilic Colloid, Product Resulting Therefrom, and Use Thereof as Displacement of Oil from Partially Depleted Reserves. |
| German DE 29 47 740 | July 3, 1980 | Verbessertes Fermentationsverfahren zur Herstellung von Xanthan. |

However, prior art processes for the large scale production of Xanthomonas heteropolysaccharides suffer from serious drawbacks due to the unique properties of these products. The heteropolysaccharides produced by the Xanthomonas culture in the fermentation medium thicken the medium itself, causing problems in oxygen transport and even in oxygen distribution in the fermentation medium. Such problems can arise even with low yields of the heteropolysaccharides.

It had been found that the application of large shear forces during fermentation suppresses the thixotropic properties of the heteropolysaccharides for a short period of time. Accordingly, the fermentation is carried out in reaction vessels, with vigorous stirring, using a flat bladed, multi-turbine mixer. When considerable stirring energy is used, it is possible to keep the reaction product, which otherwise would quickly gel, in a fluid state for a short while, thereby allowing adequate oxygen transport. In the literature, there are indications that a maximum yield of about 5 wt. % or even higher, calculated as dry substance, and based on the fermentation make-up, can be obtained. In practice, such yields are never obtained. A yield of 2–3 wt. % xanthan (dried substance) is regarded as a good yield, and yields of this magnitude will only be possible when using the above described conditions, i.e. by the use of large amounts of energy.

DESCRIPTION OF THE INVENTION

It has now been found that the use of a stable water-in-oil emulsion in the fermentation medium markedly lowers the viscosity of the medium, resulting in lower energy requirements for the process and also resulting in enhanced yields of the Xanthomonas biopolymers. In such an emulsion, the aqueous fermentation phase with its microbial growth and metabolic processes takes place in a finely dispersed homogenous "oil" phase. The viscosity increase in each droplet of the aqueous nutrient solution will not noticeably affect this mixture in the fermenter because the viscosity of the reaction mixture in the fermenter is primarily determined by the viscosity of the "oil" phase.

The water-in-oil emulsions used in the present process are used in the prior art for the manufacture of polymers or copolymers of water soluble monomers. Such prior art processes are known as inverse emulsion polymerizations. See, e.g., German patent DE-AS No. 10 89 173. However, such polymerization processes cannot be compared to a process for culturing life forms, where the presence of adequate oxygen and nutrients is required to sustain their existence and their metabolic processes.

In accordance with the present invention, the aqueous fermentation medium containing the Xanthomonas microorganisms is distributed as the dispersed phase of the emulsion. Interestingly, these microorganisms not only remain viable in the emulsions of the invention, but also retain all of their heteropolysaccharide producing capabilities. In contrast to known fermentation processes, a considerable lowering of viscosity results by use of the instant fermentation process, permitting a number of modifications and improvements over present day technology.

The "oil" phase of the water-in-oil emulsions of the present invention can be any organic liquid not freely miscible with water that is non-toxic to the Xanthomonas microorganisms, and which does not react with oxygen or other substances in the aqueous phase during the fermentation process. Preferred are organic liquids that remain in equilibrium with the aqueous phase under process conditions, and take up only limited quantities of water. It is preferred to use an organic liquid in which water is not miscible in quantities over about 0.5 wt. %, and preferably not over about 0.1 wt. %. It is also preferred to use only organic liquids that don't dissolve or produce swelling of the biopolymers produced by the process. Also, the "oil" component has to be in the liquid phase at the fermentation temperature. Preferred are organic liquids having a melting point not over about 25° C., preferably not over about 20° C., and most preferably not over about 10° C. In addition, it is preferred that the "oil" phase, under fermentation conditions, is non-volatile or is only slightly volatile. While this preferred volatility limitation is not a requirement, air flow through the fermentation mixture may remove unacceptable quantities of a more volatile organic liquid. On the other hand, following the fermentation step, a partial or total separation of the "oil" phase is desirable, and greater volatility of the organic liquid can be utilized in this separation. Accordingly, choice of the volatility of the "oil" phase can be determined in accordance with the other process conditions selected for carrying out the processes of the invention. It is understood that when the term "oil" or "oil phase" is used herein, the term will be understood to include organic liquids that are not "oils" in the classic sense.

Based on simple, initial tests, toxicological compatibility with microorganism growth for the selected oil phase can be guaranteed. Apparently, a large number of organic liquids will meet this requirement.

For the oil phase a number of hydrophobic liquids are available which can be readily separated from the liquid heteropolysaccharides produced by the processes of the invention.

Preferred are unsubstituted and/or substituted liquid hydrocarbons, either aliphatic or aromatic. The aliphatic hydrocarbons can be linear, branched, or cyclic. A single hydrocarbon or a mixture of various hydrocarbons can be used. Preferred are aliphatic hydrocarbons such as mineral oils, kerosenes, or naphtha, as well as aromatic hydrocarbons such as benzene, xylene, or toluene. Especially suitable as the oil phase are branched chain hydrocarbons, e.g. isoparaffins. Also unsubstituted or unsaturated hydrocarbon compounds such as olefinically unsaturated hydrocarbons can be employed. Also, water insoluble alcohols with 8 to 20, preferably 8 to 12 carbon atoms, vegetable oils, ester alcohols, polyethers, or other heteroatom containing compounds, such as silicon oils, can be employed herein. An isoparaffin mixture which is commercially available under the name of "ISOPAR M" can be used. A partially neutralized product consisting of water insoluble isoparaffin acids partially neutralized with hydroxy-benzyl-dialiphatic amines, described in U.S. Pat. No. 2,262,270, can also be used herein.

The aqueous fermentation medium can be selected from those known in the art for the culturing of Xanthomonas bacteria to produce heteropolysaccharides. Suitable aqueous fermentation media are given in U.S. Pat. No. 4,119,546 and in German Patent DE-OS No. 29 47 740. Typically, such nutrient media contain a source of organic nitrogen such as corn steep, and/or soya flour; phosphate salts such as di-alkali-hydrogen phosphate and/or di-ammonium hydrogen phosphate; and trace elements, especially magnesium, and sometimes even manganese, iron and calcium; at a pH above 6, preferably about 6.5 to about 7.0. The nutrient media also contains a water soluble carbohydrate. Suitable carbohydrates are e.g. glucose, saccharose, maltose, fructose, lactose, invert sugar beet molasses, invert sugar, filtered and diluted edible starches, or mixtures of such carbohydrates. Glucose is the preferred source of carbohydrate, and it is usually used in the range of 2 to 5 wt. % based on the nutrient media. Also, carbohydrates that will be assimilated during the fermentation process and which will result in increased glucose concentrations can also be added, either continuously or intermittently, during the fermentation process. The use of glucose concentrations much higher than about 5% by weight can produce an accumulation of toxic and acidic by-products, and can even inhibit the growth of the Xanthomonas bacteria. Such higher glucose concentrations can also produce an early cessation of the fermentation process.

The incubation (fermentation) temperature should be 30° C.; i.e. a temperature of 30±5° C. can be tolerated for 100 hours or longer. A process that is used commercially for the production of xanthan gum that includes reaction enhancers such as special nutrient solutions and incubation conditions is described in U.S. Pat. No. 3,236,831.

The selection of the oil phase and the aqueous nutrient solution should be made with the end use of the heteropolysaccharide in mind. For example, if xanthan gum is being produced for use in the secondary or tertiary recovery of oil deposits, the oil phase can be selected without regard to its physiological safety as a trace contaminant in the xanthan gum. On the other hand, if the xanthan gum is to be used in the food industry, the oil phase should be physiologically safe upon ingestion.

In forming the water-in-oil emulsions of the invention, the use of an emulsifier is preferred. Suitable emulsifiers are those which are soluble in the oil phase and which will form a water-in-oil emulsion when added to the aqueous phase. Such emulsifiers include sorbitol monooleate, sorbitol monostearate, hexadecyl sodium phthalate, cetyl-stearyl sodium phthalate, and other emulsifiers disclosed in German Patent DE-AS No. 10 89 173. In addition, water-in-oil emulsifying systems can be used such as the Atlas Chemie GmbH products which are sold under the trade names ARLACEL and SPAN. These products are compounds from the oleate group which contain a small quantity of TWEEN emulsifiers. Additional acceptable water-in-oil emulsifier systems are manufactured by Atlas Chemie GmbH, and are cited in the literature as "ATLAS-HLB-Systems". See also U.S. Pat. No. 3,996,186 as well as brochures from the above mentioned company that describe such systems. Numerous water-in-oil emulsifiers that can be used in the present process are listed in the Detergents and Emulsifiers Annual, published by John W. McCutcheon, Inc., Morristown, N.J.

The selection of a proper emulsifier is somewhat dependent on the process parameters selected and/or the nature of the desired biopolymer end product. Therefore, it may be possible to prepare highly stable emulsions. However, after the fermentation process has been completed, a complete separation between the oil phase and the viscous, aqueous phase might be difficult. Ideally, the emulsifier should keep the water-in-oil emulsion stable during stirring of the fermentation mixture, yet permit the emulsion to separate into two phases when stirring is discontinued at the end of the fermentation step. Also, a portion of the fermentation mixture can be removed as desired during the fermentation step, allowed to separate into two phases, and the aqueous phase returned to the fermenter.

Optional ingredients, such as dispersing agents, can also be added to the fermentation mixture as desired.

The ratios between oil phase and aqueous nutrient phase are preferably in the range of about 15 to about 90 parts by weight of the oil phase, and about 85 to about 10 parts by weight of aqueous nutrient phase at the beginning of the fermentation. More preferably, the ratio is in the range of about 20 to about 60 parts by weight of the oil phase to about 80 to about 40 parts by weight of aqueous nutrient phase, and most preferably about 25 to about 50 parts by weight of oil phase to about 75 to about 50 parts by weight of aqueous nutrient phase.

If a water-in-oil emulsifier is used in the present process, the amount used is in the range of about 0.1 to about 10 wt. %, preferably about 1 to about 5 wt. %, based on the total fermentation mixture. Also, the emulsifier content in relation to the oil phase, is advantageously in the range of from about 3 to about 20 wt. %, preferably about 5 to about 15 wt. %. The amount of emulsifier selected will depend somewhat on the chemical composition and the properties of the emulsifier. Other controlling factors include the degree of stability it is desired to impart to the water-in-oil emulsion.

Suitable Xanthomonas organisms which will produce exocellular heteropolysaccharides include the following Xanthomonas species: *Xanthomonas campestris, Xanthomas phaseoli, Xanthomonas malvacearum, Xanthomonas translucens, Xanthomonas carotae, Xanthomonas hederae, Xanthomonas papavericola, Xanthomonas pisi, Xanthomonas begoniae, Xanthomonas icanae, Xanthomonas vasculorum and Xanthomonas vesicatoria.* Preferred are the species *Xanthomonas campestris, Xanthomonas fragaria, Xanthomonas gummisudans, Xanthomonas manihotis and Xanthomonas vasculorum.*

An oxygen containing gas, most conveniently air, is added in the usual manner to the mixture in the fermenter. The oxygen requirement for the fermentation can be controlled depending on the fermentation process and the oxygen transport in order to reduce the accumulation of acidic and toxic by-products.

When compared to the usual known processes for the manufacture of xanthan gum, the present invention using water-in-oil emulsions offers the possibility of several variations in the process.

Large scale processes to grow the Xanthomonas microorganisms can be carried out in nutrient media in several stages using different compositions as described in German Patent DE-OS No. 29 74 740. The microorganisms prepared by such process are then transferred into nutrient solutions and grown therein. A variant of this invention can be utilized in the present invention, i.e. the microorganisms prepared by the above process are used to form the water-in-oil emulsions of this invention. The microorganism growth will yield the Xanthomonas heteropolysaccharide.

While the present process can be carried out by innoculating the aqueous nutrient phase with the Xanthomonas microorganism and immediately forming the water-in-oil emulsion, and then carrying out the entire fermentation process in the emulsion, it is preferred to form the emulsion after the Xanthomonas microorganisms have produced sufficient heteropolysaccharide to begin to form a gel in the aqueous nutrient medium. In particular, it is advantageous to permit microorganism growth in the aqueous nutrient medium to continue until the yield of heteropolysaccharide is at least 0.1 wt. %, and preferably until the yield is at least 0.5 wt % before forming the emulsion. The wt. % figures are the weight of the dry heteropolysaccharide compared to the weight of the aqueous fermentation medium. By using the above technique, the growth rate of the microorganisms can be increased at least 30%, and often at least 50% prior to formation of the emulsion. Initial tests can be made to determine the optimum time to form the emulsion. It has been found that a heteropolysaccharide production of 1.0 to 1.5 wt. %, sometimes as high as 2 wt. % can be obtained and still permit the ready formation of a water-in-oil emulsion.

In forming the water-in-oil emulsion, the aqueous nutrient phase and the oil phase (optionally containing a dissolved emulsifier), are mixed together and the mixture mechanically stirred and agitated. Preferably, this procedure is carried out in commercial fermenters which are equipped with heavy duty mixing units, so that thorough mixing can be obtained. Such thorough mixing insures a uniform water-in-oil emulsion, even when the emulsion would rapidly separate in the absence of stirring.

The stirred emulsion is treated by conventional means with oxygen or an oxygen containing gas, such as air. The oxygen transfer occurs across the oil phase to each individual emulsified aqueous droplet of the dispersed phase.

If needed, intermittent or continuous additions of growth stimulating agents can be added to the nutrient medium. It is, therefore, possible to gradually add carbohydrate-containing compounds such as glucose to the reaction mixture. An even distribution is assured because the nutrients are directly added to the well agitated fermenter. The addition of other constituents of the aqueous phase such as trace elements, or the addition of other needed compounds, such as bases to regulate the pH values of the dispersed aqueous phase, can also be added in this manner.

The growing stage is continued until the desired heteropolysaccharide yield is obtained or the heteropolysaccharide formation decreases or stops altogether. If an intermittent process is used, and depending on the final use of the heteropolysaccharide product, a separation of the oil phase and the heteropolysaccharide-containing dispersed phase takes place. The heteropolysaccharide can be separated by conventional means from the aqueous phase and made ready for purification. In order to break the emulsions, standard procedures used in the chemical processes industry can be employed, e.g. as disclosed in Ullman, Enzyklopadie der technischen Chemie 1975, Vol. IV, page 453, or Houben-Weyl, Methods of Organic Chemistry 1958, Vol. I/1, pp. 219/220. Breaking of the emulsion can also be achieved when adding emulsion breaking agents, or by applying mechanical forces such as high shear agitation, impacting or tension, increase of temperature, dilution or evaporation of the continuous phase, or by other well known methods. There are a number of emulsion breaking agents commercially available—see Houben-Weyl and other such sources. Normal purification procedures, such as scrubbing of the heteropolysaccharide-containing aqueous phase with selected solvents can be carried out as desired.

The present process can also be carried out by draining off some of the contents of the fermenter, either intermittently or continuously, modifying them, and recycling them back to the fermenter. For example, additional quantities of emulsifier or fresh microorganisms can be added in this manner. It is also possible to extract from this partially diverted fermentation mixture, either intermittently or continuously, the reaction products of the process. This invention, therefore, makes it possible to utilize a continuous process with continuous control of the heteropolysaccharide-containing aqueous phase, as well as continuous control of the entire process. When compared to the normal prior art processes, i.e. intermittent, single stage processes, many newer technical procedures applicable to continuous processes can be utilized, as will be apparent to those skilled in the art.

The separation of the heteropolysaccharide from the aqueous phase is done by known processes, namely by precipitation and drying. The heteropolysaccharide-containing phase can be heated to temperatures over 100° C., and immediately cooled thereafter in order to kill the Xanthomonas microorganisms and to improve the viscosity of the heteropolysaccharide. The heteropolysaccharide can be precipitated with alcohols, followed by filtration and drying steps. Wash steps to purify the heteropolysaccharide can also be carried out by known methods.

This invention will be better understood from the following examples, which are given for illustration purposes only and are not meant to limit the invention.

EXAMPLE I

*Xanthomonas campestris* NRRL-B-1459-A was aerobically grown at 27° C. in a 7 liter fermenter (5 liter volume) using the following nutrient medium:
2.80 wt. % glucose (separately sterilized)
0.60 wt. % soya flour
1.00 wt. % corn steep
0.02 wt. % $MgSO_4.7H_2O$
0.08 wt. % $(NH_4)_2HPO_4$
0.09 wt. % $Na_2HPO_4$
The pH of the nutrient medium was 6.8.

After a 24 hour incubation period, there was added an additional 2.8 wt. % of glucose. As a first control, a continuous incubation period up to a total of 64 hours was carried out while vigorously agitating the fermenter contents as well as providing uniform air ventilation, but without the addition of an oil phase. The viscosity of the fermenter contents and the xanthan yield were determined after 16, 22, 40, 47 and 60 hours incubation period. The numerical values obtained are shown in the following Table.

In a second experiment, the process of the first experiment was duplicated, including the addition of 2.8 wt. % of glucose after a 24 hour incubation period. However, after a 40 hour incubation period, a sorbitan monooleate ("SPAN 80")-containing oil phase was added, thereby forming a water-in-oil emulsion. For the oil phase, "IOSPAR M" (trade name of the Esso Chemical Company for an isoparaffin mixture in the boiling range of 200 to to 250? C., and containing 0.3 wt. % of an aromatic substance) was used. The amount of oil phase was 30 wt %, based on the total mixture. The emulsifier content was 3 wt. %.

The viscosity and xanthan yield in this experiment were determined after 16, 22, 40, 47, and 64 hours incubation periods. The following Table lists and compares the results obtained:

TABLE

| Fermentation-Conditions | Incubation Period (Hrs.) | Viscosity[1] (c.P.) | xanthan Yield[2] (g/l) |
|---|---|---|---|
| Control make-up | 16 | 650 | — |
| | 22 | 1,700 | 8.3 |
| | 40 | 7,300 | 16.0 |
| | 47 | 9,200 | 19.0 |
| | 64 | 10,000 | 18.2 |
| Emulsion make-up when 3% SPAN 80 plus 30% ISOPAR M was added after 40 hours incubation | 16 | 850 | — |
| | 22 | 2,400 | 12.3 |
| | 40 | 9,500 | 17.9 |
| | 40 | 500[3] | — |
| | 47 | 750 | 20.0 |
| | 64 | 500 | 25.5 |

[1]Brookfield Viscosimeter, Spinelle 2 - 5, Velocity 20.
[2]Dry weight after precipitation.
[3]After adding SPAN 80 and ISOPAR M.

The control make-up shows that under the above process conditions, the xanthan production, after a 47 hour incubation period, practically stops. In contrast, the emulsion make-up according to this invention will maintain a significant increase in xanthan production with an incubation period from 47 to 67 hours as compared to the initial phase of the growing cycle (incubation period 22 to 40 hours). When adding an oil phase after a 40 hour incubation period, the viscosity of the fermenter contents decreases in the present process to its initial value, and will not increase in spite of continuous xanthan growth.

A third experiment was carried out in the same manner as in the second experiment. After a 24 hour incubation period, 2.8 wt. % glucose was added, and after a 40 hour incubation period, "SPAN 80" was added together with 30 wt. % of "ISOPAR M" as the oil phase. The amount of "SPAN 80" added was 1.5 wt. %. This experiment produced a xanthan yield of 25 g/l.

EXAMPLE II

*Xanthomonas campestris* NRRL-B-1459-A was grown in the same manner as in the second experiment of EXAMPLE I, except that the following oil phase was used to form an emulsion after 40 hours incubation:
2.2 wt. % glycerin stearate (ATMOS 300)
4.4 wt. % polyoxyethyleneoleyl ether (BRIJ 92)
43.4 wt. % isotridecylstearate (RILANIT ITS)
A xanthan yield of 24.5 g/l was obtained.

What is claimed is:

1. In the method of conducting a fermentation reaction wherein an aqueous culture medium comprising a carbohydrate source and a nitrogen source is inoculated with a polysaccharide gum producing Xanthomonas microorganism and said medium is mechanically agitated and aerated under conditions to effect fermentation thereof, the improvement which comprises said culture medium being dispersed via a surfactant in about 15 to about 90%, based on the total weight of dispersion, of a water insoluble oil in which the resultant polysaccharide is also insoluble.

2. The method of claim 1, wherein the water insoluble oil is a hydrocarbon or a mixture of hydrocarbons.

3. The method of claim 1, wherein the water insoluble oil is a mineral oil.

4. The method of claim 1, wherein from about 20 to about 60% by weight of a water insoluble oil is present.

5. The method of claim 1, wherein from about 25 to about 50% by weight of a water insoluble oil is present.

6. The method of claim 1, wherein the surfactant is present in from about 0.1 to about 10% by weight based on the total weight of dispersion.

7. The method of claim 6, wherein from about 1 to about 5% by weight of surfactant is present.

8. The method of claim 1, wherein the water insoluble oil has a melting point that does not exceed about 25° C.

9. The method of claim 1, wherein the Xanthomonas microorganism is first grown for a period of time in an aqueous culture medium, followed by the addition of the surfactant and the water insoluble oil to form a water-in-oil dispersion, and the growth of the microorganism is continued.

10. The method of claim 1, wherein the microorganism is *Xanthomonas campestris*.

* * * * *